United States Patent [19]
Tso et al.

[11] Patent Number: 5,527,533
[45] Date of Patent: Jun. 18, 1996

[54] METHOD OF RETARDING AND AMELIORATING CENTRAL NERVOUS SYSTEM AND EYE DAMAGE

[75] Inventors: Mark O. M. Tso, Northbrook; Tim-Tak Lam, Skokie, both of Ill.

[73] Assignee: Board of Trustees of the University of Illinois, Urbana, Ill.

[21] Appl. No.: 330,194

[22] Filed: Oct. 27, 1994

[51] Int. Cl.$^6$ .................................................. A61K 31/00
[52] U.S. Cl. .................... 424/422; 424/427; 514/912; 514/913; 514/914; 514/915; 514/929
[58] Field of Search .................... 424/59, 60, 78.04, 424/427; 128/645; 514/912, 913, 914, 915, 929; 568/378

[56] References Cited

U.S. PATENT DOCUMENTS 3,920,834  11/1975  Kläui et al. ............................ 424/59
5,243,094   9/1993  Borg .................................... 568/822

FOREIGN PATENT DOCUMENTS 467795  1/1992  European Pat. Off.

OTHER PUBLICATIONS

Li et al., *Current Eye Research*, vol. 10(2), 1991, pp. 133–144.
Johnson et al., *Applied. Envirn. Micro.*, vol. 35(6), 1978 pp. 1155–1159.
Anon., "Bio & High Technology Announcement Itaro", Itaro Refrigerated Food Co., Ltd.
Anon., "Natural Astaxanthin & Krill Lecithin", Itaro Refrigerated Food Co., Ltd.
DiMascio, P. et al., "Carotenoids, Tocopherols and Thiols as Biological Singlet Molecular Oxygen Quenchers", *Biochemical Society Transactions*, 18, pp. 1054–1056 (1990).
Hiramitsu, T. et al., "Preventative Effect of Antioxidants on Lipid Peroxidation in the Retina", *Ophthalmic Res.*, 23, pp. 196–203 (1991).
Johnson, E. A. et al., "Simple Method for the Isolation of Astaxanthin from the Basidomycetous Yeast *Phaffia rhodozyma*", *App. Environ. Microbiol.*, 35(6), pp. 1155–1159 (1978).
Kirschfeld, K., "Carotenoid Pigments: Their Possible Role in Protecting Against Photooxidation in Eyes and Photoreceptor Cells", *Proc. R. Soc. Lond.*, B216, pp. 71–85 (1982).
Krinsky, N. I. et al., "Interaction of Oxygen and Oxy-radicals With Carotenoids", *J. Natl. Cancer Inst.*, 69(1), pp. 205–210 (1982).
Kurashige, M. et al., "Inhibition of Oxidative Injury of Biological Membranes by Astaxanthin", *Physiol. Chem. Phys. and Med. NMR*, 22 pp. 27–38 (1990).
Latscha, T., "Carotenoids-Carotenoids in Animal Nutrition", Hoffmann-LaRoche Ltd., Basel, Switzerland.
Li, Z. et al., "Desferrioxime Ameliorated Retinal Photic Injury in Albino Rats", *Current Eye Res.*, 10(2), pp. 133–144 (1991).
Mathews-Roth, M., "Porphyrin Photosensitization and Carotenoid Protection in Mice; In Vitro and In Vivo Studies", *Photochemistry and Photobiology*, 40(1), pp. 63–67 (1984).
Mathews-Roth, M., "Carotenoids and Cancer Prevention--Experimental and Epidemiological Studies", *Pure and Appl. Chem.*, 57(5), pp. 717–722 (1985).
Mathews-Roth, M., "Recent Progress in the Medical Applications of Carotenoids", *Pure and Appl. Chem.*, 63(1), pp. 147–156 (1991).

(List continued on next page.)

*Primary Examiner*—Thurman K. Page
*Assistant Examiner*—Pamela S. Webber
*Attorney, Agent, or Firm*—Marshall, O'Toole, Gerstein, Murray & Borun

[57] ABSTRACT

A method of retarding and ameliorating eye diseases and injuries is disclosed. The method comprises administering astaxanthin in a therapeutically-effective amount to prevent, retard or treat eye and central nervous system diseases or injuries, such as age-related macular degeneration and other central nervous system degenerative diseases, photic injury, ischemic diseases, and inflammatory diseases.

27 Claims, 4 Drawing Sheets

OTHER PUBLICATIONS

Michon, J. J. et al., "A Comparative Study of Methods of Photoreceptor Morphometry", *Invest. Ophthalmol. Vis. Sci.*, 32, pp. 280–284 (1991).

Miki, W., "Biological Functions and Activities of Animal Carotenoids", *Pure and Appl. Chem.*, 63(1), pp. 141–146 (1991).

Schalch, W., "Carotenoids in the Retina–A Review of Their Possible Role in Preventing or Limiting Damage Caused by Light and Oxygen", *Free Radicals and Aging*, I. Emerit et al. (ed.), Birkhauser Verlag, pp. 280–298 (1992).

Tso, M.O.M., "Experiments on Visual Cells by Nature and Man: In Search of Treatment for Photoreceptor Degeneration", *Investigative Ophthalmology and Visual Science*, 30(12), pp. 2421–2454 (Dec. 1989).

Tso, M.O.M., "Pathogenetic Factors of Aging Mascular Degeneration",*Ophthalmology*,92(5), pp. 628–635 (1985.

Yu, D. et al., "Amelioration of Retinal Photic Injury by Beta–Carotene", *ARVO Abstracts Invest. Ophthalmol. Vis. Sci.*, 28 *(Suppl.)*, p. 7, (1987).

METHOD OF RETARDING AND AMELIORATING CENTRAL NERVOUS SYSTEM AND EYE DAMAGE

FIELD OF THE INVENTION

The present invention relates to a method of retarding and ameliorating central nervous system and eye diseases. More particularly, the present invention is directed to methods of treating central nervous system and eye insult resulting from disease or injury, such as age-related macular degeneration, photic injury, photoreceptor cell or ganglion cell damage, traumatic injury, ischemic insult-related diseases and inflammatory diseases. The method comprises administering a therapeutically-effective amount of astaxanthin to an individual, either orally, topically or parenterally, to ameliorate damage caused by the disease or injury or to retard the progress of a degenerative disease.

BACKGROUND OF THE INVENTION

Many diseases and injuries of the central nervous system presently are not treatable. These diseases and injuries are untreatable because, unlike many peripheral organs that can be removed in whole or in part, or transplanted, the central nervous system has very limited regeneration capability and cannot be totally excised without death. The eye is an extension of the brain, and therefore a part of the central nervous system. Accordingly, in the case of an eye injury or disease, i.e., a retinal injury or disease, the diseases are often without treatment and the eye cannot be transplanted. Eye diseases and injuries that presently are untreatable include retinal photic injury, retinal ischemia-induced eye injury, age-related macular degeneration, and other eye diseases and injuries that are induced by free radical species.

It has been hypothesized that a major cause of these untreatable central nervous system diseases and injuries is the generation and presence of singlet oxygen and other free radical species. Singlet oxygen and free radical species can be generated by a combination of light and oxygen, or during reperfusion after an ischemic insult.

The eye is subjected to continuous light exposure because the primary purpose of the eye is light perception. Therefore, some untreatable diseases and injuries to the eye result from the continuous exposure of the eye to light, coupled with the highly-oxygenated environment in the eye.

The process of light perception is initiated in the photoreceptor cells. The photoreceptor cells are a constituent of the outer neuronal layer of the retina, which is a component of the central nervous system. The photoreceptor cells are well sheltered in the center of the eye, and are protected structurally by the sclera, nourished by the highly-vascularized uvea and safeguarded by the blood-retinal barrier of the retinal pigment epithelium.

The primary function of the photoreceptor cells is to convert light into a physio-chemical signal (transduction) and to transmit this signal to the other neurons (transmission). During the transduction and transmission processes, the metabolic activities of these neurons are changed dramatically. Even though the photoreceptor cells are securely protected in the interior of the eye, these cells are readily accessible to light because their primary function is light detection. Excessive light energy reaching the retina can cause damage to these neurons, either directly or indirectly, by overwhelming the metabolic systems of these cells.

The combination of continuous and/or excessive exposure to light, and the relatively high concentration of oxygen in the eye, generates singlet oxygen and other free radical species. Singlet oxygen and free radical species also can be generated by enzymatic processes independent from light exposure. The free radical species and singlet oxygen are reactive entities that can oxidize polyunsaturated fatty acids. The retina contains the highest concentration of polyunsaturated fatty acids of any tissue in the human body, and peroxidation of the polyunsaturated fatty acids in cell membranes of the retina by hydroxyl radicals (OH) or superoxide ($O_2$) radicals can propagate additional free radical species. These free radical species can lead to functional impairment of the cell membranes and cause temporary or permanent damage to retinal tissue. It has been theorized that the generation of singlet oxygen and free radical species therefore underlies the pathogenesis of light-induced retinopathy and post-ischemic reflow injury (i.e., free radical generation during reperfusion after an ischemic insult). In addition, a deficiency in removing these species can also contribute to various diseases of the eye and the central nervous system.

A number of natural mechanisms protect the photoreceptor cells from light injury. For example, the ocular media, including the cornea, aqueous, lens, and vitreous, filter most of the light in the ultraviolet region. However, after cataract extraction or other surgical intervention, some of these protective barriers are removed or disturbed, whereby the photoreceptor cells are more susceptible to damage by radiant energy. The photoreceptor cells also possess other forms of protection from photic injury, for example, the presence of antioxidant compounds to counteract the free radical species generated by light. As will be demonstrated hereafter, antioxidants, which quench and/or scavenge singlet oxygen, hydrogen peroxide, superoxide and radical species, help minimize injury to the photoreceptor cells. In addition, the human eye has an excessive number of photoreceptor cells such that only destruction of a significant number of photoreceptor cells adversely affects visual function.

Even though several protective mechanisms are present in the eye, a leading cause of blindness in the United States is age-related photoreceptor degeneration. Clinically, photoreceptor degeneration, as seen in age-related macular degeneration, is causally related to excessive exposure to blue light. The causes of age-related macular degeneration, which is characterized by a loss of photoreceptor neurons resulting in decreased vision, are being investigated. Epidemiological studies indicate that age-related photoreceptor degeneration, or age-related macular degeneration, is caused by several factors including age, sex, family history, color of the iris, nutritional deficiency, immunologic disorders, cardiovascular and respiratory diseases and preexisting eye diseases. Advancing age is the most significant factor. Recently, it has been demonstrated that aging eyes have a decreased amount of carotenoids. Clinical and laboratory studies indicate that photic injury is a cause of age-related macular degeneration because of the cumulative effect of repeated mild photic insult which leads to a gradual loss of photoreceptor cells.

Age-related macular degeneration is an irreversible blinding disease of the retina. Unlike cataract wherein vision can be restored by replacing the diseased lens, age-related macular degeneration cannot be treated by replacing the diseased retina because the retina is a component of the central nervous system. Therefore, because no treatment for this disease exists once the photoreceptors are destroyed, prevention is the only way to confront age-related macular degeneration. Presently, prevention of age-related macular degeneration resides in limiting or preventing light and oxygen-induced (i.e., free radical-induced) damage to the retina because the retina is the only organ that is continuously exposed to high levels of light in a highly-oxygenated environment.

In addition to photic injury, eye injury and disease can result from singlet oxygen and free radical species generated during reperfusion after an ischemic insult. Ischemic insult to retinal ganglion cells and to neurons of the inner layers of retina causes loss of vision. Loss of vision accompanies diabetic retinopathy, retinal arterial occlusion, retinal venous occlusion and glaucoma, each of which ischemically insults the eye, i.e., deprives the eye of oxygen and nutrition.

The damage to the retinal ganglion cells has been attributed to ischemia, and subsequent reperfusion during which free radicals are generated. During reperfusion, the reoxygenation of tissue after an ischemic insult results in a relatively high concentration of oxygen flowing through the effected tissue, which contributes to free radical formation. Ischemic insult and reperfusion accompanied by free radical generation also is a major contributor to central nervous system damage, such as damage caused by a stroke.

The pathogenesis of photic injury, of age-related macular degeneration, of ischemia/reperfusion damage, of traumatic injury and of inflammations of the eye and central nervous system have been attributed to singlet oxygen and free radical generation, and subsequent free radical-initiated reactions. Investigators therefore studied the role of antioxidants in preventing or ameliorating these diseases and injuries of the central nervous system in general, and the eye in particular.

For example, ascorbate was investigated as an agent to treat retinal photic injury. Ascorbate is a reducing agent which is present in the retina in a high concentration. Studies indicated that ascorbate in the retina can act as an antioxidant and is oxidized by free radical species generated during excessive light exposure.

Administration of ascorbate reduced the loss of rhodopsin after photic exposure, thereby suggesting that ascorbate offered protection against retinal photic injury. A decrease in rhodopsin levels is an indicator of photic eye injury. The protective effect of ascorbate is dose-dependent, and ascorbate was effective when administered before light exposure. Morphometric studies of the photoreceptor nuclei remaining in the retina after light exposure showed that rats given ascorbate supplements had substantially less retinal damage. Morphologically, rats with ascorbate supplements also showed better preservation of retinal pigment epithelium.

The above studies led to the hypothesis that ascorbate mitigates retinal photic injury because of its antioxidant properties, which are attributed to its redox properties. Ascorbate is a scavenger of superoxide radicals and hydroxy radicals and also quenches singlet oxygen and reduces hydrogen peroxide, all of which are formed in retinal photic injury. This hypothesis accounts for the presence of high levels of naturally-occurring ascorbate in a normal retina.

Therefore, antioxidants which inhibit free radical formation, or which quench singlet oxygen and scavenge for free radical species, can decrease lipid peroxidation and ameliorate photic injury and ischemic/reperfusion injury in the central nervous system, and particularly in the retina. Antioxidants originally were investigated because they are known constituents of human tissue. However, antioxidants that are not naturally occurring in human tissue also were tested. In particular, in addition to ascorbate, antioxidants such as 2,6-di-tert-butylphenol, γ-oryzanol, α-tocopherol, mannitol, reduced glutathione, and various carotenoids have been studied for an ability to quench singlet oxygen and scavenge free radical species. These and other antioxidants are effective quenchers and scavengers for singlet oxygen and free radicals. In particular, the carotenoids, as a class of compounds, are very effective singlet oxygen quenchers and free radical scavengers. However, individual carotenoids differ in their ability to quench singlet oxygen and scavenge for free radical species.

The carotenoids are naturally-occurring compounds that have antioxidant properties. The carotenoids are common compounds manufactured by plants or animals, and contribute greatly to the coloring of plants and animals. A number of animals, including mammals, are unable to synthesize carotenoids de novo and accordingly rely upon diet to provide carotenoid requirements. Mammals also have a limited ability to modify carotenoids. A mammal can convert β-carotene to vitamin A, but most other carotenoids are deposited in mammalian tissue in unchanged form.

With respect to humans, about ten carotenoids are found in human serum. The major carotenoids in human serum are β-carotene, α-carotene, cryptoxanthin, lycopene and lutein. Small amounts of zeaxanthin, phytofluene, and phytoene are found in human organs. However, of the ten carotenoids found in human serum, only two, zeaxanthin and lutein, are found in the human retina. Zeaxanthin is the predominant carotenoid in the macula and is concentrated in the cone cells in the center of the retina, i.e., the macula. Lutein is located in the peripheral retina in the rod cells. Therefore, the eye preferentially assimilates zeaxanthin over lutein in the macula and also selectively concentrates zeaxanthin, which is a more effective singlet oxygen scavenger than lutein, in the center of the eye. It has been theorized that zeaxanthin and lutein are concentrated in the retina because of their ability to quench singlet oxygen and scavenge free radicals, and thereby limit or prevent photic damage to the retina.

Therefore only two of the about ten carotenoids present in human serum are found in the retina. Beta-carotene and lycopene, the two most abundant carotenoids in human serum, either have not been detected or have been detected only in minor amounts in the retina. Beta-carotene is relatively inaccessible to the retina because β-carotene is unable to cross the blood-retinal brain barrier of the retinal pigment epithelium effectively. As will be explained in detail hereinafter, small amounts of β-carotene have been found to cross the blood-retinal brain barrier.

It also is known that another carotenoid, canthaxanthin, can cross the blood-retinal brain barrier and reach the retina. Canthaxanthin, like all carotenoids, is a pigment and can discolor the skin. Canthaxanthin provides a skin color that approximates a suntan, and accordingly has been used by humans to generate an artificial suntan. However, an undesirable side effect in individuals that ingested canthaxanthin at high doses for an extended time was the formation of crystalline canthaxanthin deposits in the inner layers of the retina. Therefore, the blood-retinal brain barrier of the retinal pigment epithelium permits only particular carotenoids to enter the retina. The carotenoids other than zeaxanthin and lutein that do enter the retina cause adverse effects, such as the formation of crystalline deposits by canthaxanthin, which may take several years to dissolve. Canthaxanthin in the retina also caused a decreased adaptation to the dark.

Investigators have unsuccessfully sought an antioxidant to counteract the adverse affects of singlet oxygen and free radical species on the central nervous system in general and the eye in particular. The investigators have studied the antioxidant capabilities of several compounds, including various carotenoids. Even though the carotenoids are strong antioxidants, investigators have failed to find particular carotenoids among the 600 naturally-occurring carotenoids that effectively quench singlet oxygen and scavenge for free radical species, that are capable of crossing the blood-retinal brain barrier, that do not exhibit the adverse affects of canthaxanthin after crossing the blood-retinal brain barrier, and that ameliorate central nervous system or eye disease or injury and/or retard the progression of a degenerative disease of the central nervous system or eye.

Various publications are directed to eye diseases and injuries, such as age-related macular degeneration, causes of the damage resulting from the diseases or injuries, and attempts to prevent or treat such diseases and injuries. The publications, which discuss various antioxidants, including the carotenoids and other antioxidants like α-tocopherol, include:

M. O. M. Tso, "Experiments on Visual Cells by Nature and Man: In Search of Treatment for Photoreceptor Degeneration", *Investigative Ophthalmology and Visual Science*, 30(12), pp. 2421–2454 (December, 1989);

W. Schalch, "Carotenoids in the Retina—A Review of Their Possible Role in Preventing or Limiting Damage Caused by Light and Oxygen", *Free Radicals and Aging*, I. Emerit et al. (ed.), Birkhauser Verlag, pp. 280–298 (1992);

M. O. M. Tso, "Pathogenetic Factors of Aging Macular Degeneration", *Ophthalmology*, 92(5), pp. 628–635 (1985);

M. Mathews-Roth, "Recent Progress in the Medical Applications of Carotenoids", *Pure and Appl. Chem.*, 63(1), pp. 147–156 (1991);

W. Miki, "Biological Functions and Activities of Animal Carotenoids", *Pure and Appl. Chem.*, 63(1), pp. 141–146 (1991);

M. Mathews-Roth, "Carotenoids and Cancer Prevention-Experimental and Epidemiological Studies", *Pure and Appl. Chem.*, 57(5), pp. 717–722 (1985);

M. Mathews-Roth, "Porphyrin Photosensitization and Carotenoid Protection in Mice; In Vitro and In Vivo Studies", *Photochemistry and Photobiology*, 40(1), pp. 63–67 (1984);

P. DiMascio et al., "Carotenoids, Tocopherols and Thiols as Biological Singlet Molecular Oxygen Quenchers", *Biochemical Society Transactions*, 18, pp. 1054–1056 (1990);

T. Hiramitsu et al., "Preventative Effect of Antioxidants on Lipid Peroxidation in the Retina", *Ophthalmic Res.*, 23, pp. 196–203 (1991);

K. Kirschfeld, "Carotenoid Pigments: Their Possible Role in Protecting Against Photooxidation in Eyes and Photoreceptor Cells", *Proc. R. Soc. Lond.*, B216, pp. 71–85 (1982);

D. Yu et al., "Amelioration of Retinal Photic Injury by Beta-Carotene", *ARVO Abstracts Invest. Ophthalmol. Vis. Sci.*, 28 (Suppl.), p. 7, (1987);

M. Kurashige et al., "Inhibition of Oxidative Injury of Biological Membranes by Astaxanthin", *Physiol. Chem. Phys. and Med. NMR*, 22, pp. 27–38 (1990); and N. I. Krinsky et al., "Interaction of Oxygen and Oxyradicals With Carotenoids", *J. Natl. Cancer Inst.*, 69(1), pp. 205–210 (1982).

In general, the above-identified publications support the hypothesis that singlet oxygen and free radical species are significant contributors to central nervous system, and particularly eye, injury and disease. For example, it has reported that consumption of an antioxidant, such as ascorbic acid (Vitamin C), α-tocopherol (Vitamin E) or β-carotene, can decrease the prevalence of age-related macular degeneration.

The above-identified publications also demonstrated that several carotenoids, including astaxanthin, are strong antioxidants compared to β-carotene, ascorbic acid and other widely used antioxidants. The publications also relate that (1) only particular carotenoids selectively cross the blood-retinal brain barrier, and that (2) certain carotenoids other than zeaxanthin and lutein that cross the blood-retinal brain barrier cause adverse affects.

In general, the above-identified publications teach that astaxanthin is a more effective antioxidant than carotenoids such as zeaxanthin, lutein, tunaxanthin, canthaxanthin and β-carotene, and than α-tocopherol. For example, the in vitro and in vivo studies disclosed in the Kurashige et al. publication with respect to astaxanthin demonstrated that the mean effective concentration of astaxanthin which inhibits lipid peroxidation was 500 times lower than that of α-tocopherol. Similarly, the Miki publication discloses that, in vitro, astaxanthin exhibits a strong quenching effect against singlet oxygen and a strong scavenging effect against free radical species.

Investigators have theorized that free radical-mediated reactions are involved in the pathogenesis of degenerative diseases, such as Alzheimer's disease, Parkinson's disease and age-related macular degeneration, ischemic/reperfusion damage and traumatic injury of the brain, spinal cord and retina, as well as in inflammatory processes of the body, and particularly the eye. This theory has been advanced by investigators examining the effectiveness of various antioxidants in ameliorating these diseases. For example, methylprednisolone, which at high doses is a strong lipid peroxidation inhibitor, has been recommended clinically for use in traumatic injury of the spinal cord.

To date, investigative efforts have been directed to preventing diseases and injury because the resulting free radical-induced damage is not effectively treatable. Therefore, a need exists for a method not only to prevent or retard, but also to ameliorate, degenerative and traumatic diseases and injuries to the central nervous system, and particularly the eye. The present invention is directed to such methods.

SUMMARY OF THE INVENTION

The present invention is directed to methods of treating individuals suffering from central nervous system injury or disease. More particularly, the present invention is directed to methods of treating individuals suffering from an eye injury or disease, and to methods of retarding a degenerative disease of the eye.

The method comprises administering a therapeutically-effective amount of astaxanthin to an individual to retard a degenerative disease, or to ameliorate damage to the central nervous system caused by a disease or an injury. In particular, the method comprises administering a therapeutically-effective amount of astaxanthin to an individual to beneficiate the vision of an individual suffering from eye damage caused by disease or injury. The astaxanthin can be administered parenterally, orally or topically.

The method is used to treat free radical-induced eye damage, light-induced eye damage, photoreceptor cell damage, ganglion cell damage, damage to neurons of inner retinal layers, and age-related macular degeneration. The present method also ameliorates neuronal damage to the retina, wherein the neuronal damage is a result of photic injury, or ischemic, inflammatory or degenerative insult.

One aspect of the present invention is to administer about 5 to about 500 milligrams (mg) of astaxanthin, and preferably about 10 to about 200 mg, per kilogram (kg) of body weight per dose, to retard a degenerative disease of the central nervous system or the eye, or to ameliorate damage resulting from an injury or a disease of the central nervous system or the eye.

Another aspect of the present invention is to provide a method of treating an inflammatory disease of the eye by administering a therapeutically-effective amount of astaxanthin to an individual.

Another aspect of the present invention is to treat diseases and injuries to the central nervous system by administering a therapeutically-effective amount of astaxanthin to an individual. The method is used to treat diseases and injuries effecting the brain, eye and spinal cord, such as injury caused by spinal cord trauma or by a stroke or neurodegenerative diseases.

These and other novel features and aspects of the present invention will become apparent from the following detailed description of the preferred embodiments taken in conjunction with the figures.

DETAILED DESCRIPTION OF THE PREFERRED EMBODIMENTS

Figure 1:
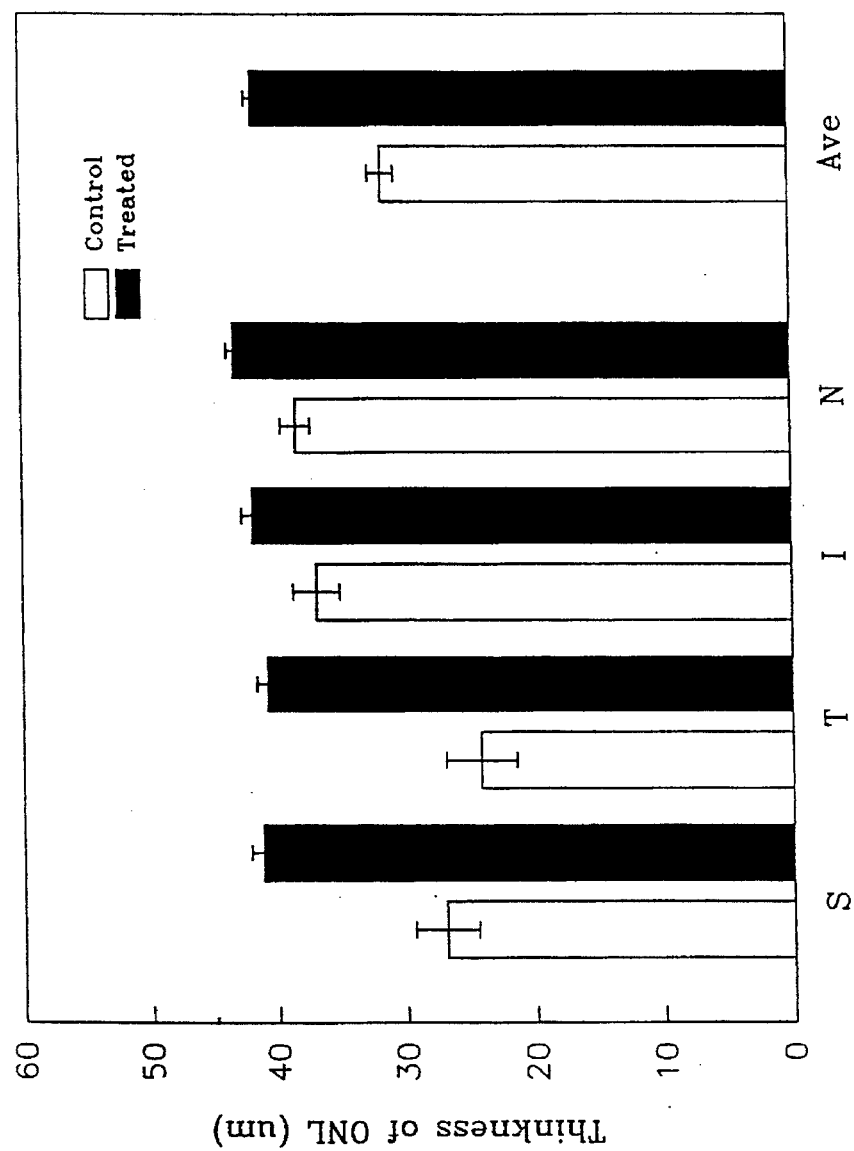
FIG. 1 is a bar graph showing the thickness of the ONL (outer nuclear layer) of the retina in micrometers ($\mu$m) after light-induced receptor degeneration, and comparing the retinas of control animals to the retinas of animals treated with astaxanthin given parenterally both for the retina as a whole (average) and for each of the four quadrants of the retina.

Certain diseases and injuries to the central nervous system, and particularly the eyes, presently are untreatable. Neuronal degeneration of the central nervous system or the eye can result from photic injury, ischemic or intraocular pressure-related insult, e.g., an occlusion or a stroke, or from a trauma, e.g., trauma to the spinal cord. The damage also can result from injury to the photoreceptor cells, to the ganglion cells in the retina of the eye or to neurons in the inner retinal layers of the eye, or from age-related macular degeneration.

It has been theorized that the damage from such diseases and injuries can be attributed to increased generation, or decreased removal, of singlet oxygen and free radical species. Therefore, because antioxidants are known to quench singlet oxygen and to scavenge for free radical species, and because antioxidants are known to exist in humans, investigators have sought effective antioxidants to scavenge free radicals, and thereby reduce the free radical-induced damage caused to the central nervous system, and especially to the eye, by disease and injury.

Numerous antioxidants have been investigated, such as for example, ascorbic acid, $\alpha$-tocopherol and $\beta$-carotene. Some investigators have focused on the carotenoids, e.g., $\beta$-carotene, because over 600 carotenoids are known, are naturally occurring (and therefore are abundant), and are strong antioxidants. Also, with respect to the eyes, two carotenoids, zeaxanthin, and lutein, which are strong antioxidants, are found in the photoreceptor cells of the retina. However, although human plasma includes about ten carotenoids, only these two carotenoids are able to effectively cross the blood-retinal brain barrier and concentrate in the macula of the eye. Beta-carotene, the most abundant human plasma carotenoid, has a very limited ability to cross the blood-retinal brain barrier.

The ability of a carotenoid to pass the blood-retinal brain barrier is important because carotenoids are not synthesized by the human body. The only source of carotenoids for humans is dietary intake. Furthermore, humans have a very limited ability to modify carotenoids. Therefore, the carotenoids accumulate in various organs in the ingested form. Accordingly, if a particular carotenoid is unable to cross the blood-retinal brain barrier, the carotenoid cannot accumulate in the retina and serve as an antioxidant.

Furthermore, carotenoids that are not normal constituents of human plasma, but have an ability to cross the blood-retinal brain barrier, have demonstrated adverse affects on the retina. Canthaxanthin which is intentionally ingested to provide an artificial suntan has accumulated in the retina in the form of crystals and has temporarily affected eye adaptation to the dark. In addition, $\beta$-carotene has a limited ability to cross the blood-retinal brain barrier.

Therefore, even though the carotenoids are known as strong antioxidants and are present in abundant supply, the carotenoids have not been used for the treatment of central nervous system damage, or eye damage, caused by disease or injury. The carotenoids investigated to date either could not effectively cross the blood-retinal barrier (i.e., $\beta$-carotene) or adversely affected the eye (i.e., canthaxanthin.

In accordance with an important feature of the present invention, astaxanthin, which is a naturally-occurring compound and is a potent antioxidant, is used in a method to ameliorate and retard, or prevent, cell damage in an individual suffering from a degenerative, inflammatory or traumatic disease or injury to the central nervous system, and particularly to the eye. In accordance with another important feature of the present invention, the administration of a therapeutically-effective amount of astaxanthin to an individual prevents, retards and/or ameliorates free radical-induced damage resulting from disease or injury, such as a trauma. For example, damage to a retina can result from either photic injury, neurodegenerative disease or an ischemic insult followed by reperfusion. With respect to damage from photic injury, astaxanthin decreases the loss of photoreceptor cells. With respect to damage from ischemic insult, astaxanthin ameliorates the loss of ganglion cells and the inner layers of the retinal neuronal network.

In general, the carotenoids are terpenoid compounds which are widely-distributed in nature, and which selectively absorb light. About 600 carotenoids have been isolated and identified from various vegetable and animal sources. Animals cannot synthesize carotenoids de novo, but rely upon plant sources. Therefore, animals rely on dietary intake for carotenoids. Animals however can modify carotenoids. The ability to modify carotenoids is very limited in humans.

Carotenoids are classified into two major groups: (1) the carotenes, which are hydrocarbons, and (2) the xanthophylls, which include oxygen in addition to carbon and hydrogen. The xanthophylls can be considered oxidation products of the carotenes, and are prepared by the insertion of oxygen into carotenes and subsequent rearrangements. The most common carotenoid is the carotene, β-carotene. The following illustrates the chemical structure of various carotenoids:

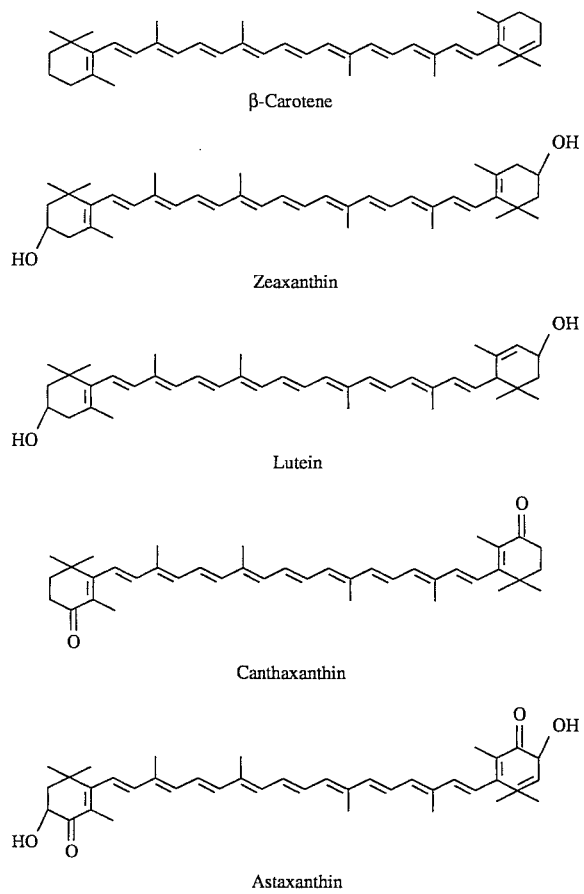

The chemical structures of the five above carotenoids illustrate that minor changes in chemical structure greatly affect the properties of the carotenoid, such as the ability of the carotenoid to cross the blood-retinal brain barrier and the ability of the carotenoid to act as an antioxidant. For example, β-carotene is the most abundant carotenoid in human plasma, but typically is not found in the retina. Small amounts of β-carotene are found in the retina if β-carotene is administered in high doses intraperitoneally or orally. These results indicate that β-carotene has great difficulty in crossing the blood-retinal brain barrier. In contrast, zeaxanthin and lutein, both of which are very similar in structure to β-carotene, are concentrated in the retina even though zeaxanthin and lutein are present in only minor amounts in human plasma.

With respect to an ability to act as an antioxidant, the carotenoids differ greatly with respect to an ability to quench singlet oxygen and scavenge for free radicals. The above-identified DiMascio publication reported the following ability of carotenoids to quench singlet oxygen:

astaxanthin>canthaxathin>β-carotene>zeaxanthin>lutein>>α-tocopherol.

The above-identified Miki publication reported the following ability of carotenoids to scavenge for free radical species:

astaxanthin>zeaxanthin>canthaxanthin>lutein>β-carotene>α-tocopherol.

Therefore minor structural differences affect the ability of a carotenoid to act as an antioxidant in general, and more particularly to act as a singlet oxygen quencher or a free radical scavenger.

Canthaxanthin, which is a strong antioxidant and which has a structure similar to zeaxanthin and lutein, has the ability to cross the blood-retinal brain barrier. However, canthaxanthin accumulates in the retina to form crystals. Astaxanthin also has a structure similar to canthaxanthin, zeaxanthin and lutein. Astaxanthin also is a stronger antioxidant than canthaxanthin, zeaxanthin and lutein. Surprisingly, astaxanthin, which is not present in human plasma, was found to have the ability to cross the blood-retinal brain barrier (unlike β-carotene), but does not form crystals in the retina and does not otherwise adversely affect the eye (unlike canthaxanthin).

Astaxanthin, or 3,3'-dihydroxy-β,β-carotene-4,4'-dione, is an abundant, naturally-occurring compound. Astaxanthin is the major pigment of crustaceans, and is the most widely distributed xanthophyll in the animal kingdom.

Astaxanthin is a lipid-soluble pigment primarily used for pigmenting cultured fish, like salmon, which must ingest astaxanthin to yield consumer-acceptable pink-colored salmon muscle. Astaxanthin also is an antioxidant which is about 100 to about 1000 times more effective than α-tocopherol.

The prime source of astaxanthin is shells of crustaceans, like krill. Astaxanthin also is available synthetically. Either the naturally-occurring or the synthetic astaxanthin can be used in the composition and method of the present invention.

In particular, astaxanthin is presently available in three forms: (1) natural astaxanthin extracted from krill, available from Itano Refrigerated Food Co., Tokushima, Japan; (2) synthetic astaxanthin available from Itano Refrigerated Food Co.; and (3) astaxanthin extracted from *Phaffia Rhodozyma* yeast, available from Universal Food Co., Milwaukee, Wis. However, astaxanthin in any available form would be used in the method of the present invention. In the following experiments, the astaxanthin extracted from krill was used as received. The synthetic astaxanthin first was mixed with soy bean oil before use. The yeast-based astaxanthin was extracted with acetone to enrich the astaxanthin content. The astaxanthin-rich extract then was mixed with soy bean oil before use.

As previously stated, the retinal pigment epithelium protects the retina by providing a blood-retinal brain barrier. The barrier excludes plasma constituents that are potentially harmful to the retina. As also previously stated, the blood-retinal brain barrier only permits lutein and zeaxanthin to enter the retina, and excludes other carotenoids present in human serum, including β-carotene which is the most abundant carotenoid in human serum. Therefore, an experiment was performed to determine whether astaxanthin, which is not a component of human plasma, has the ability to cross the blood-retinal brain barrier.

To determine whether astaxanthin has the ability to cross the blood-retinal brain barrier and concentrate in the retina of a mammal, an astaxanthin solution was prepared by suspending 0.15 g (grams) of AST-5000, an astaxanthin extracted from krill and available from Itano Refrigerated Food Co., in 1.0 mL (milliliters) of a 1.0% by weight aqueous solution of TWEEN-80 (polyoxyethylene sorbitan monooleate, available from Sigma Chemical Co., St. Louis Mo.). The resulting astaxanthin solution (1.5 mL) was injected intraperitoneally into six (6) rats. After euthanizing the rats, the retinas were examined for the presence of astaxanthin. After six consecutive intraperitoneal injections of astaxanthin at twelve hour intervals and at a dose of about 37.5 mg/kg of body weight provided an average concentration of astaxanthin in the retina of about 0.17 µg/mg (micrograms per milligram) wet tissue 6 hours after the last injection.

Astaxanthin is not a naturally-occurring constituent in the retina. Therefore, the presence of such a significant amount of astaxanthin in the retina illustrates the ability of astaxanthin to readily cross the blood-retinal brain barrier into the retina.

The ability of astaxanthin to ameliorate eye damage caused by photic injury was demonstrated as follows:

Light-induced photoreceptor degeneration was conducted according to the protocol reported in Z. Li et al., *Current Eye Res.*, 10, pp. 133–44 (1991), incorporated herein by reference. Briefly, seven 35 to 40-day old male albino Lewis rats (Harlan, Indianapolis, Ind.) were fed a normal diet and placed on a twelve hour cycle of light (uniform illuminance of 53.8 lux) and darkness for 14 days. Pour rats then were administered four intraperitoneal injections of a suspension of 0.15 g of AST-5000 (astaxanthin) in 1.0 mL of aqueous 1.0% TWEEN-80. The dose of each injection was 37.5 mg astaxanthin/kg of body weight per injection. The injections were administered at 12 hour intervals starting at 24 hours before light exposure. Three control rats were injected with 1.0 mL of all aqueous 1.0% TWEEN-80 solution. All seven rats were exposed to 180–200 ft-candle (1800 to 2000 lux), green-filtered fluorescent light (490–580 nm) (Plexiglass No. 2092, Polycast technology, Stamford, Conn.) for 24 hours after one day of total dark adaptation. All seven rats were kept in the dark for a two-day recovery period, then euthanized with an overdose of pentobarbital. Both eyes of each rat were enucleated for histopathologic and morphometric studies.

The enucleated eyes of each rat were fixed in a 0.1M phosphate-buffered 4% formaldehyde and 1% glutaraldehyde solution (by weight). The anterior segment of each eye was removed, and the posterior segment was divided into the superior (S), nasal (N), inferior (I), and temporal (T) quadrants. Tissue samples from each quadrant then were osmicated (i.e., treated with osmic acid), dehydrated in a graded series of alcohols, and embedded in an epoxy resin. Morphologic and morphometric studies were performed on 1 µm (micrometer) sections stained with Mallory's azure II-methylene blue.

A quantitative determination of photoreceptor cell degeneration was made by measuring the thickness of the outer nuclear layer (ONL) of the retina by a masked observer, as described in J. Michon et al., *Invest. Ophthalmol. Vis. Sci.*, 32, pp. 280–84 (1991), incorporated herein by reference. The measurements were made with an image processing system wherein the stained retinal sections were projected onto a digitizing pad coupled to a microcomputer. The measurements were made from the posterior pole to the ora serrata on two sections.

The bar graphs of FIG. 1 summarize the results of the photic injury test. From FIG. 1, for each quadrant and for the retina as whole, the ONL thickness of the retina was greater for rats receiving the astaxanthin injection. The astaxanthin therefore protected the photoreceptors in each of the four eye quadrants, and in the whole eye as well. For example, the ONL for the whole eye of rats receiving the astaxanthin was about 42 µm thick. The ONL of the whole eye of the control rats was about 32 µm thick. For comparison, in the absence of a photic injury, the ONL of a normal eye is about 45 µm thick. FIG. 1 therefore shows that the administration of astaxanthin provides significant protection to photoreceptor cells from photic injury.

The ability of astaxanthin to ameliorate injury to neurons after retinal ischemic insult and subsequent reperfusion was demonstrated as follows:

Two 45 to 50-day old male albino Lewis rats (Harlan, Indianapolis, Ind.) were administered three intraperitoneal injections of a suspension of 0.15 g of AST-5000 (astaxanthin) in 1.0 mL of 1.0% aqueous TWEEN-80 (i.e., a dose 37.5 mg/kg/injection). Two other albino rats were injected with 1.0 mL solution of 1.0% aqueous TWEEN-80 as a control. The injections were administered at 12 hour intervals starting at 24 hours before retinal ischemic insult. Two additional rats were used as untreated controls.

Four rats were anesthetized with an intraperitoneal injection of chloral hydrate (400 mg/kg). Then, bilateral ischemic insult was induced by elevating intraocular pressure (IOP) through an infusion cannula to the anterior chamber. The IOP was maintained at 110 mm (millimeter) Hg for 60 minutes. Then, the cannulas were removed, and reperfusion of ocular vessels was established by fundus examination. All four rats were euthanized 7 days after reperfusion with an overdoes of pentobarbital. Both eyes of each rat were enucleated and fixed in a 0.1M phosphate buffer and 1% glutaraldehyde and 4% formaldehyde solution (by weight).

After the anterior segment of each eye was removed, the posterior segment of each fixed enucleated eye was divided into the superior (S), temporal (T), inferior (I) and nasal (N) quadrants. A strip from each quadrant was sampled, processed and embedded in epoxy resin. Morphologic and morphometric evaluations were performed on 1 µm sections stained with methylene blue. The degree of ischemic insult was evaluated by measuring the average thickness (IRT) between the internal limiting membrane (ILM) to the interface of the outer plexiform layer (OPL) and the outer nuclear layer (ONL). The measurements were taken on the projected image of the stained retinal sections with the aid of image processing. Measurements from all quadrants of the retina were averaged to obtain a mean value for IRT per eye.

Figure 2:
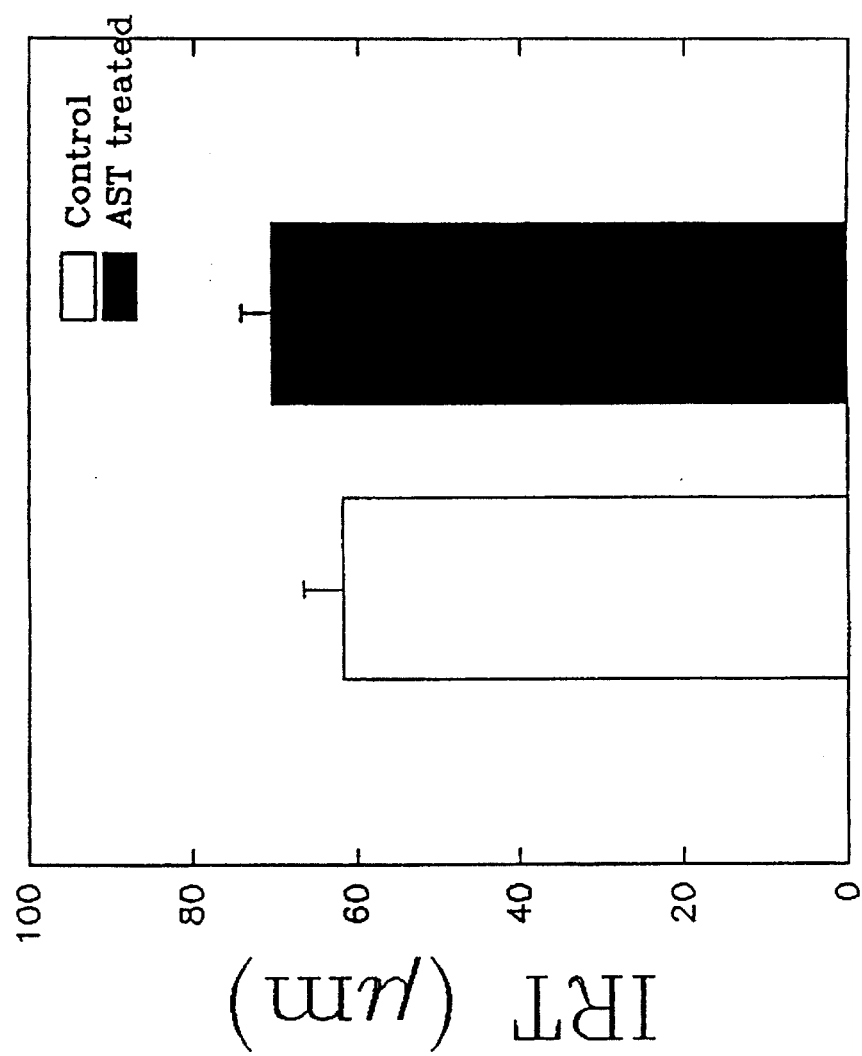
FIG. 2 is a bar graph showing the thickness of the inner retinal layer (IRL) in micrometers comparing the retinas of control animals to the retinas of animals after ischemic insult treated with astaxanthin.

The bar graph of FIG. 2 summarizes the results of the ischemic insult test. From FIG. 2, it is observed that the average IRT of the retinae of rats treated with astaxanthin was greater than the IRT of the control rats, seven days after retinal ischemic insult.

The IRT for rats treated with astaxanthin was about 70 µm. The IRT for the control rats was about 62 µm. for comparison, the normal IRT for a rat that was not subjected to retinal ischemic insult was 120 µm. The astaxanthin-treated rats, having an IRT about 10 µm thicker than the untreated rats, demonstrated that astaxanthin provided statistically-significant protection to the ganglion cells and other neuronal elements of the inner retina from ischemic insult.

In addition to tests using astaxanthin obtained by the extraction of krill, tests also were performed using astaxanthin extracted from *Phaffia Rhodozyma*. The astaxanthin was extracted using a modification of the procedure disclosed by E. A. Johnson et al., *App. Environ. Microbiol.*, 35, pp. 1155–59 (1978), incorporated herein by reference. One hundred grams of dried *Phaffia Rhodozyma* powder (Universal Food Co., Milwaukee, Wis.) was mixed and ground with 200 ml water containing 70 mg of butylated hydroxytoluene (BHT). The slurry was extracted by adding 2 L of acetone containing 0.7 gram BHT. The resulting mixture was stirred at room temperature for one hour, then centrifuged at 3,110 g for 10 minutes. The supernatant liquid was separated from the solid material, then evaporated with a rotary evaporator. The residue then was extracted again with 1 L acetone using the same procedure as the first extraction. The residue of the acetone extractions then was dissolved in 100 ml acetone containing 35 mg of BHT. The resulting suspension was air dried and stored at $-20°$ C. until use. The astaxanthin content of the extract was about 10% by weight (by high pressure liquid chromatography).

Photic injury was induced in 35 to 40 day-old male albino Lewis rats (Harlan, Indianapolis, Ind.) fed a normal diet. The rats were subjected to a 12-hour cycle of light (uniform illuminance of 53.8 lux) and darkness for 14 days. The animals then were given a daily oral feeding of either: (1) the extracted astaxanthin in 1.0 mL of soy bean oil at a dose of 80 mg astaxanthin/kg/day or (2) 1.0 mL of soy bean oil as a control, starting nine days before light exposure and continuing for eleven days. A group of eighteen rats was fed the extracted astaxanthin, and a second group of another eighteen rats was fed the soy bean oil control. All thirty-six rats were exposed to 180–200 ft-candle (1800 to 2000 lux) green filtered fluorescent light (490–580 nm) (Plexiglass No. 2092, Polycast technology, Stamford, Conn.) for 24 hours after one day of total dark adaptation. All thirty-six rats were kept in the dark for a 6 hour, 6 day, or 13 day recovery periods, then euthanized with an overdose of pentobarbital. One eye of each rat was enucleated for histopathologic and morphometric studies. The second eye of each rat was used for biochemical evaluation of rhodopsin levels.

Therefore, one enucleated eye of each rat was fixed in 0.1M phosphate-buffered 4% formaldehyde and 1% glutaraldehyde solution (by weight). The anterior segment of each eye was removed, and the posterior segment was divided into the superior (S), nasal (N), inferior (I), and temporal (T) quadrants. Tissue samples from each quadrant then were osmicated, dehydrated in a graded series of alcohols, and embedded in an epoxy resin. Morphologic and morphometric studies were performed on 1 µm sections stained with Mallory's azure II-methylene blue.

A quantitative determination of photoreceptor cell injury was made by measuring the thickness of the outer nuclear layer (ONL) of the retina by a masked observer, as described in the Michon et al. publication incorporated herein by reference. The measurements were made with an image processing system wherein stained retinal sections were projected onto a digitizing pad coupled to a microcomputer. The measurements were made from the posterior pole to the ora serrata on two sections per quadrant.

The second enucleated eye of each rat was used to estimate the retinal rhodopsin levels in accordance with the published method in Z. Li et al., *Current Eye Res.*, 10, pp. 133–44 (1991), incorporated herein by reference. Rhodopsin is a light-sensitive protein found in the rods of the retina in the eye. A decrease in rhodopsin pigment level is indicative of photic injury to the eye. A retina that has not been subjected to photic injury has a rhodopsin level of about 2 to about 2.25 nmol (nanomoles) per eye.

Figure 3:
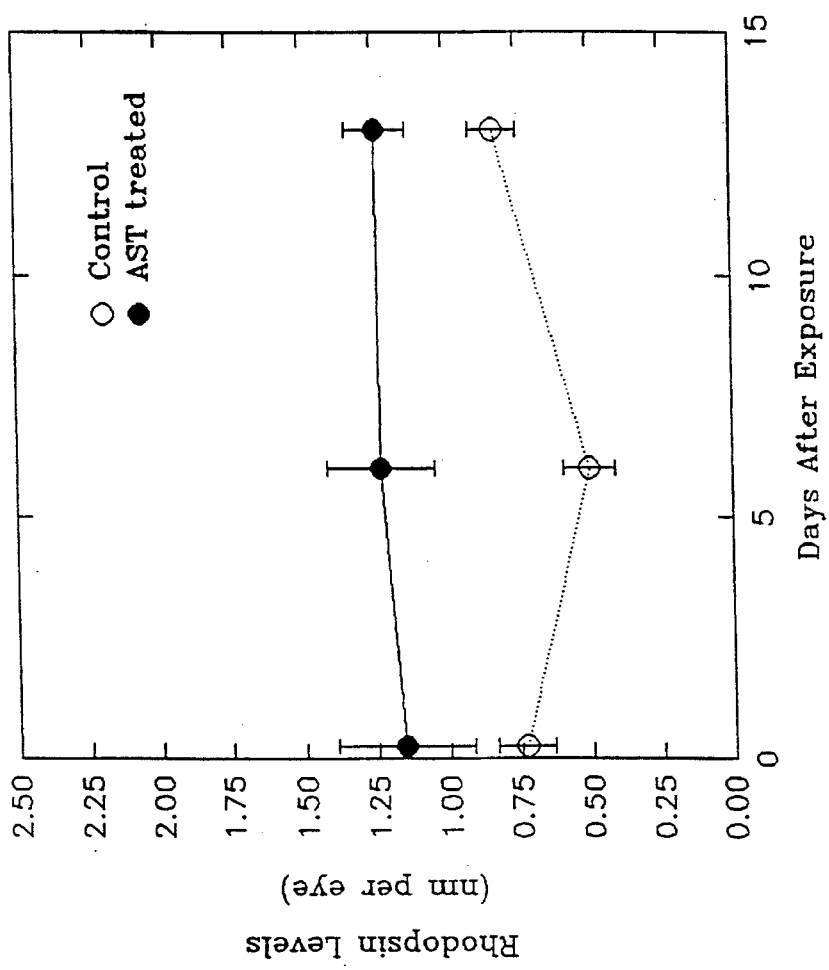
FIG. 3 is a plot of rhodopsin level vs. time after photic injury comparing the retinas of animals treated orally with astaxanthin to the retinas of control animals.

FIG. 3 summarizes the results of this photic injury test. The plots in FIG. 3 show that the rhodopsin level in the retinas of control rats continues to fall for six days following the photic injury, then the rhodopsin level rises. The rhodopsin level of control rats is about 0.75 nmol six hours after photic injury, drops to about 0.5 nmol six days after photic injury, then improves to about 0.8–0.85 nmol thirteen days after photic injury.

In contrast, the astaxanthin-treated rats had a rhodopsin level of about 1.15–1.2 nmol six hours after photic injury. In addition, the rhodopsin level did not decrease over the next six days, but increased to about 1.25 nmol then remained essentially constant through day thirteen after photic injury.

Therefore, astaxanthin not only protected the photoreceptor cells from photic injury (i.e., greater level of rhodopsin six hours after photic injury) but also ameliorated the effects of the photic injury because rhodopsin levels did not fall for a period of six days after the photic injury, but increased.

A similar test was performed wherein β-carotene was injected into rats, and rhodopsin levels in the retinae of the euthanized rats were determined. Rats were given four intraperitoneal injections of β-carotene at a dose of 35 kg/mg. A control group of rats also was used. After exposure to continuous green-filtered fluorescent light with an intensity of 220–250 foot-candles for 24 hours, the rhodopsin level was measured as an indication of photic injury. The β-carotene-treated rats had rhodopsin levels of 1.18, 0.20, and 0.55 nmol, six hours, six days and thirteen days, respectively, after photic injury. The results show that astaxanthin is more effective than β-carotene. It is hypothesized, but not relied upon herein, that these comparative results between astaxanthin and β-carotene is attributed to the antioxidant properties of astaxanthin and the ability of astaxanthin to cross the blood-retinal barrier.

The tests using β-carotene show that six hours after light injury there was considerable loss of photoreceptor nuclei in both the control and treated rats. Six to fourteen days after light exposure there was a difference between the control animals and the treated animals, with the treated animals being less affected. The treated rats demonstrated better preservation of the photoreceptor nuclei and retinal pigment epithelium in all quadrants. Beta-carotene therefore ameliorated photic injury in rat retina. However, β-carotene has difficulty crossing the blood-retinal brain barrier. Astaxanthin both crosses the blood-retinal brain barrier more easily than β-carotene, and has not demonstrated a tendency to form crystals in the retina.

Figure 4:
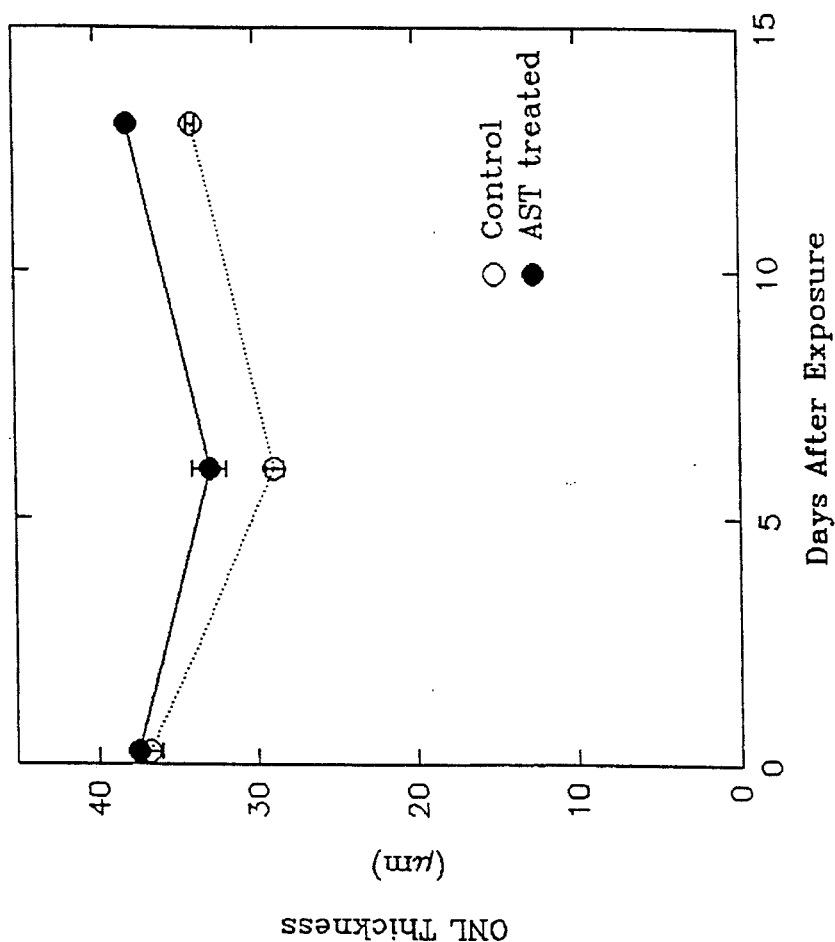
FIG. 4 is a plot of ONL thickness vs. time after photic injury comparing the retinas of animals treated orally with astaxanthin to the retinas of control animals.

FIG. 4 also summarizes the results of the above-described photic injury test. FIG. 4 includes plots of the average thickness of the ONL over a period of thirteen days after the photic injury. Rats fed astaxanthin had photic damage ameliorated compared to the control rats. The rats fed astaxanthin did not exhibit as large a decrease in ONL six days after photic injury, and exhibited a greater ONL, by about 5 µm, thirteen days after photic injury. The tests illustrated in FIGS. 3 and 4 also show that astaxanthin can be administered orally, as well as intraperitoneally to ameliorate eye damage.

The in vivo test results illustrated in FIGS. 1–4 show the ability of astaxanthin to protect neurons and neuronal elements of the inner and outer retina from photoreceptor cell degeneration in the retina and from ischemic and intraocular pressure-related injury to neurons of the inner layers of retina. The tests have shown that astaxanthin can protect or rescue neurons and other cell types, and that astaxanthin is an effective therapeutic agent to ameliorate photoreceptor degeneration and ischemic damage to neurons of the retina. In addition, astaxanthin has a protective effect on the central nervous system in general, especially damage to the brain and spinal cord caused by free radicals.

The above tests show that the administration of a therapeutically-effective amount of astaxanthin to an individual prevents, retards and/or ameliorates damage to the central nervous system, and especially to the eye, resulting from disease or injury. The astaxanthin is administered to the individual in doses of about 5 to about 500 mg (milligram) astaxanthin per kilogram (kg) of body weight. Preferably, the astaxanthin dose is about 10 to about 200 mg astaxanthin per kg of body weight, and to achieve the full advantage of the present invention, the astaxanthin dose is about 25 to about 150 mg astaxanthin/kg of body weight. The optimal astaxanthin dose can be determined by a person skilled in the art after considering factors such as the disease or injury to be treated, the severity of the central nervous system damage, and the route of administration (i.e., oral, topical or parenterally). The astaxanthin doses can be administered daily or in accordance with a regimen determined by a person skilled in the art, with the length of treatment depending upon the severity and nature of the injury to the central nervous system.

The astaxanthin can be administered to an individual parenterally, orally or topically. When administered orally, the astaxanthin can be, for example, in the form of a liquid preparation, a tablet or as a component of food. When applied topically, the astaxanthin can be, for example, in the form of an eye drop composition for direct application to the eyes.

The administration of astaxanthin to an individual suffering from an eye injury or disease, such as free radical-induced injury, beneficiates the vision of the individual by rescuing further photoreceptor cells from damage destruction. The free radical-induced damage can be attributed to light-induced injury or to injury resulting from an ischemic insult and subsequent reperfusion or neurodegenerative diseases. The administration of astaxanthin also helps prevent and retard photic injury in addition to ameliorating photic injury.

The administration of astaxanthin ameliorates photoreceptor cell damage that is light induced, and ameliorates ganglion cell damage that is induced by ischemic insult and subsequent reperfusion. The administration of astaxanthin also retards the progress of degenerative eye diseases and beneficiates the vision of individuals suffering from a degenerative eye disease, such as age-related macular degeneration.

The administration of astaxanthin also provides a method of treating ischemic retinal diseases, such as diabetic retinopathy, cystoid macular edema, central retinal arterial occlusion, central retinal venous occlusion and glaucoma. In addition, astaxanthin administration is useful in treating inflammatory diseases of the eye such as retinitis, uveitis, iritis, keratitis and scleritis wherein free radicals are produced in abundance. These ischemic retinal diseases and inflammatory diseases of the eye are free radical related. Therefore, the antioxidant properties of astaxanthin, coupled with the ability of astaxanthin to cross the blood-retinal brain barrier, lack of toxicity of astaxanthin, and the lack of adverse side effects associated with astaxanthin, make astaxanthin a useful compound to treat or prevent such free radical-related diseases.

Because astaxanthin is a highly-effective antioxidant and ameliorates free radical-induced eye damage, the administration of astaxanthin also provides a method of treating free radical-induced disease or injury to the central nervous system in general. For example, a therapeutically-effective amount of astaxanthin can be administered to stroke victims to ameliorate the ischemic insult-related injury attributed to the stroke. Astaxanthin also can be administered to individuals suffering from a traumatic injury to the spinal cord which leads to free radical-induced damage.

Investigators have long searched for effective antioxidants that can ameliorate neuronal damage. A suitable antioxidant must have the ability to cross the blood-retinal brain barrier, and must have a low toxicity. Of the several antioxidants tested to date, the antioxidant either could not effectively pass the blood-retinal brain barrier (e.g., β-carotene) or are toxic or exhibited adverse side effects (e.g., canthaxanthin). Astaxanthin is a natural, nontoxic product, and to date has not been shown to be toxic or exhibit adverse side effects even after the administration of large doses of astaxanthin for prolonged time periods. For example, astaxanthin has not demonstrated the disadvantageous side effects of closely-structurally related canthaxanthin and β-carotene with respect to forming crystals in the retina or decreasing adaptation to the dark.

Because no effective and nontoxic compound has been found for preserving neurons from various types of injury or disease, there is no established medical treatment for diseases such as age-related macular degeneration. The only active therapy is administration of β-carotene and ascorbic acid. However, β-carotene cannot effectively cross the blood-retinal brain barrier. Ascorbic acid is naturally present in the retina. Surprisingly, astaxanthin is a strong antioxidant and can effectively cross the blood-retinal brain barrier to serve in the treatment for age-related macular degeneration. The finding that the administration of astaxanthin also protects photoreceptors from degeneration also provides a method of treating diseases and injuries to the central nervous system which heretofore have been unavailable.

Obviously, may modifications and variations of the invention as hereinbefore set forth can be made without departing from the spirit and scope thereof and therefore only such limitations should be imposed as are indicated by the appended claims.

We claim:

1. A method of treating an individual suffering from retinal damage or retinal disease, said method comprising administering a therapeutically effective amount of astaxanthin to the individual to improve the vision of the individual.

2. The method of claim 1 wherein the astaxanthin is administered parenterally.

3. The method of claim 1 wherein the astaxanthin is administered orally.

4. The method of claim 1 wherein the astaxanthin is administered topically directly to the eye.

5. The method of claim 1 wherein the astaxanthin is administered in the amount of about 5 to about 500 milligrams per kilogram of body weight.

6. The method of claim 1 wherein the astaxanthin is administered in the amount of about 10 to about 200 milligrams per kilogram of body weight.

7. The method of claim 1 wherein the astaxanthin is administered in the amount of about 25 to about 150 milligrams per kilogram of body weight.

8. The method of claim 1 wherein the retinal damage comprises free radical-induced retinal damage.

9. The method of claim 1 wherein the retinal damage comprises light-induced retinal damage.

10. The method of claim 1 wherein the retinal damage comprises photoreceptor cell retinal damage or damage to neurons of inner retinal layers.

11. The method of claim 1 wherein the retinal damage comprises ganglion cell retinal damage.

12. The method of claim 1 wherein the retinal damage comprises age-related macular degeneration.

13. A method of treating an individual comprising administering a therapeutically effective amount of astaxanthin to the individual to protect neurons in a retina of the individual from free-radical induced retinal injury.

14. A method of treating an individual suffering from neuronal damage to a retina comprising administering a therapeutically-effective amount of astaxanthin to the individual to improve the condition of the retina.

15. The method of claim 14 wherein the neuronal damage comprises photic injury to the retina, ischemic insult to the retina, or intraocular pressure-related insult to the retina.

16. A method of treating an individual suffering from age-related macular degeneration comprising administering a therapeutically-effective amount of astaxanthin to the individual to retard the progress of age-related macular degeneration.

17. A method of treating an individual suffering from an ischemic or intraocular pressure-related disease of a retina comprising administering a therapeutically-effective amount of astaxanthin to the individual to improve the condition of the retina and to prevent further damage to the retina.

18. The method of claim 17 wherein the ischemic retinal disease is selected from the group consisting of diabetic retinopathy, cystoid macular edema, central retinal arterial occlusion, central retinal venous occlusion, and glaucoma.

19. A method of treating an individual suffering from an inflammatory disease of a retina comprising administering a therapeutically effective amount of astaxanthin to the individual to improve the condition of the retina and to prevent further damage to the retina.

20. The method of claim 19 wherein the inflammatory disease is selected from the group consisting of retinitis, uveitis, iritis, keratitis, and scleritis.

21. A method of treating an individual suffering from a free radical-induced injury to a central nervous system, said method comprising administering a therapeutically-effective amount of astaxanthin to the individual to improve the condition of the central nervous system.

22. The method of claim 21 wherein the central nervous system comprises a brain, a spinal cord and a retina.

23. The method of claim 22 wherein the free radical-induced injury comprises a traumatic injury or an ischemic injury.

24. The method of claim 23 wherein the ischemic injury comprises a stroke.

25. The method of claim 23 wherein the traumatic injury comprises a spinal cord injury.

26. A method of treating an individual suffering from a degenerative retinal disease, said method comprising administering a therapeutically effective amount of astaxanthin to the individual to retard the progress of the disease.

27. A method of treating an individual suffering from a degenerative central nervous system disease of a brain or spinal cord, said method comprising administering a therapeutically effective amount of astaxanthin to the individual to retard the progress of the disease.

* * * * *

UNITED STATES PATENT AND TRADEMARK OFFICE
CERTIFICATE OF CORRECTION

PATENT NO. : 5,527,533

DATED : June 18, 1996

INVENTOR(S) : Mark O.M. Tso et al.

It is certified that error appears in the above-identified patent and that said Letters Patent is hereby corrected as shown below:

Column 11, line 25, "Pour" should be --Four--.

Column 12, line 28, "overdoes" should be --overdose--.

Column 16, line 27, "may" should be --many--.

Signed and Sealed this

Fifteenth Day of October, 1996

Attest:

BRUCE LEHMAN

*Attesting Officer*          *Commissioner of Patents and Trademarks*

(12) INTER PARTES REVIEW CERTIFICATE (105th)
United States Patent
Tso et al.

(10) Number: US 5,527,533 K1
(45) Certificate Issued: Sep. 22, 2015

(54) METHOD OF RETARDING AND AMELIORATING CENTRAL NERVOUS SYSTEM AND EYE DAMAGE

(75) Inventors: Mark O. M. Tso; Tim-Tak Lam

(73) Assignee: BOARD OF TRUSTEES OF THE UNIVERSITY OF ILLINOIS

Trial Numbers:

IPR2013-00401 filed Jun. 28, 2013
IPR2013-00404 filed Jun. 29, 2013

Petitioner: Cyanotech Corporation

Patent Owner: The Board of Trustees of The University of Illinois

Inter Partes Review Certificate for:

Patent No.: 5,527,533
Issued: Jun. 18, 1996
Appl. No.: 08/330,194
PCT Filed: Oct. 27, 1994

The results of IPR2013-00401 and IPR2013-00404 are reflected in this inter partes review certificate under 35 U.S.C. 318(b).

INTER PARTES REVIEW CERTIFICATE
U.S. Patent 5,527,533 K1
Trial No. IPR2013-00401
Certificate Issued Sep. 22, 2015

AS A RESULT OF THE INTER PARTES REVIEW PROCEEDING, IT HAS BEEN DETERMINED THAT:

Claims 15, 21 and 22 are found patentable.

Claims 1-14 and 26 are cancelled.

\* \* \* \* \*